United States Patent [19]
Mendes et al.

[11] Patent Number: 5,683,436
[45] Date of Patent: Nov. 4, 1997

[54] TREATMENT OF RHINITIS BY BIOSTIMULATIVE ILLUMINATION

[75] Inventors: Emanuel Mendes, Petach Tikva; Ittai Neuman, Carmei Yosef, both of Israel

[73] Assignee: Amron Ltd., Tel Aviv, Israel

[21] Appl. No.: 292,717

[22] Filed: Aug. 18, 1994

[30] Foreign Application Priority Data

Feb. 24, 1994 [IL] Israel .................................. 108772

[51] Int. Cl.$^6$ .................................................. A61N 5/06
[52] U.S. Cl. .................................................. 607/88; 607/90
[58] Field of Search .................................. 607/88–90, 92; 128/633, 664–666; 606/2, 3, 12, 13; 362/80 R

[56] References Cited

U.S. PATENT DOCUMENTS

| | | | |
|---|---|---|---|
| 4,926,880 | 5/1990 | Claude et al. | 607/150 |
| 4,930,504 | 6/1990 | Diamantopoulos et al. | 607/88 |
| 4,931,053 | 6/1990 | L'Esperance, Jr. | 606/2 |
| 4,963,798 | 10/1990 | McDermott | 362/800 |
| 5,259,380 | 11/1993 | Mendes | 607/115 |
| 5,304,207 | 4/1994 | Stromer | 607/88 |
| 5,335,659 | 8/1994 | Pologe | 128/633 |
| 5,358,503 | 10/1994 | Bertwell et al. | 607/88 |
| 5,384,693 | 1/1995 | Schwaller et al. | 362/184 |

FOREIGN PATENT DOCUMENTS

| | | | |
|---|---|---|---|
| 2212016 | 7/1989 | United Kingdom | 607/88 |
| 9415666 | 7/1994 | WIPO | 607/88 |

OTHER PUBLICATIONS

Abstract, Kruchinina et al, "Effect of Laser Therapy on Local Immunoglobin Synthesis in Children with Acute or Chronic Maxillary Sinusitis," Vestn Otorinolaringiolog, vol. 2, 1988, pp. 19–21.

Abstract, Pluzhnikov, "Use of Intracavity Low–Energy Laser Theray in the Complex Treatment of Inflammatory Diseases of the Sphenoid Sinus", Vestn Otorinolaringoliolog, vol. 4, Jul.–Aug. 1986, pp. 72–73.

Abstract, Kaiser et al, "Helium–Neon Laser radiation versus Placebo in the treatment of Acute Maxillary Sinusitis", Av Odontoestoestomatol, Mar.–Apr. 1987, vol. 3, No. 2, pp. 73–76.

Abstract, Moustsen et al "Laser Treatment of Sinusitis in General Practice Assessed by Double–Blind Controlled Study", Egeskr Laeger, Aug. 5, 1991, vol. 153(32) pp. 2232–2234.

Benefit/Risk Ratio of the Antihistamines . . . (Medline abstract) Simons–FE; *Reggin–JD;* Roberts–JR; Simons–KJ J–Pediatr. 1994 Jun; 124 (6) : 979–83.

Effect of Low–Power Density Laser Radiation . . . (Medline abstract) Kana–JS; Hutschenreiter–G; Haina–D; Waidelich–W Arch–Surg. 1981 Mar.; 116(3) : 293–6.

The In–vivo–nerve Response to Direct Low–Energy–Laser . . . (Medline abstract) Rochkind–S; Nissan–M; Lubart–R; Avram–J; Bartal–A Acta–Neurochir––Wien. 1988; 94(1–2) : 74–7.

Effects of Visible and Near–Infrared Lasers . . . (Medline abstract) Lubart–R; Wollman–Y; Friedman–H; Rochkind–S; Laulicht–I J–Photochem–Photobiol–B. 1992 Feb. 28: 12 (3) : 305–310.

(List continued on next page.)

*Primary Examiner*—Robert L. Nasser
*Attorney, Agent, or Firm*—Natter & Natter

[57] ABSTRACT

Apparatus for treating rhinitis by illumination including at least one light emitting diode (LED) pack, each having a plurality of light emitting diodes (LEDs), suitable for insertion into at least one, respective, rhinitis affected nostril and operative for illuminating a rhinitis affected zone of the interior surface of the at least one nostril with non-coherent light radiation, the light radiation having a narrow bandwidth centered at a wavelength suitable for rhinitis treatment. Preferably, the rhinitis affected zone is illuminated continuously for a prescribed treatment duration.

28 Claims, 4 Drawing Sheets

OTHER PUBLICATIONS

Changes in Oxidative Metabolism of Murine . . . (Medline abstract) Karu–T; Andreichuk–T; Ryabykh–T Lasers–Surg–Med. 1993; 13 (4): 453–62.

Photoreactivation of Superoxide Dismutase . . . (Medline abstract) Vladimirov–YA; Gorbatenkova–EA; Paramonov–NV; Azizova–OA Free–Radic–Biol–Med. 1988; 5 (5–6): 281–6.

Endoscopic Endonasal Surgery . . . (Medline abstract) Stammberger–H Otolaryngol–Head–Neck–Surg. 1986 Feb.; 94 (2): 143–7.

Molecular Mechanism of Therapeutic Effect of Low Intensity Laser Radiation Karu, T.I.; Lasers in Life Sciences 2 (1) 1988 pp.53–74.

Photobiological Basis of Low Level Laser Radiation Therapy.

American Society for Laser Medicine and Surgery Abstracts Lasers in Surgery and Medicine, Supplement 3, 1991 pp. 9–12.

The Biomedical Effects of Laser Application Mester, Andre; Mester, Andrew and Mester, Adam; Lasers in Surgery and Medicine 5:31–39 (1985).

A Possible Explanation of Laser Induced Stimulation Friedman, H.; Lubart, R. and Laulicht, I.; Journal Photochemistry B; Biol (1991) 87–95.

Towards an Explanation of Visible and Infrared Laser Induced Stimulation . . . Friedman, H. and Lubart, R.; Laser Therapy (1992) pp. 39–42.

Macrophage Responsiveness to Light Therapy Young, S.; Bolton, P.; Dyson, M. et al. Lasers in Surgery and Medicine 9:487–505 (1989).

TREATMENT OF RHINITIS BY BIOSTIMULATIVE ILLUMINATION

FIELD OF THE INVENTION

The present invention relates to light therapy in general and, more particularly, to devices and methods for treating the rhinitis.

BACKGROUND OF THE INVENTION

Clinical symptoms of rhinitis such as a runny nose, an itchy nose, post nasal drainage of mucus and, in extreme cases, congested secondary air passages, may be attributed to various etiologies. The common etiologies are viral infection, such as infectious rhino sinusitis. Other etiologies include allergic, perennial, or seasonal rhinitis, also known as "hay fever", non allergic vasomotor rhinitis, eosinophyllic rhinitis and nasal polyps.

Existing methods of treatment of the above mentioned rhinitis symptoms include systematic use of medications, such as antihistamines and decongestants, or local treatment with steroid spray, D.S.C.G. or local decongestants. There have been also attempts to treat rhinitis locally by applying a "fog stream", i.e. a stream of water at a temperature of approximately 42° C.

It is appreciated that none of the existing treatments described above, nor any combinations thereof, completely relieve rhinitis related symptoms. Therefore, a large population is helplessly exposed to the irritating discomforts of rhinitis symptoms.

Light therapy is known for treating a variety of patient complaints and ailments. A state of the art device suitable for administering light therapy is disclosed in U.S. Pat. No. 4,930,504 to Diamantopoulos et al. Diamantopoulos et al hypothesize that the disclosed device may be used, "for example, to treat inflammations, wounds, burns, chronic ulcerations including diabetic ulcers, deficient circulation, pain, nerve degeneration, eczema, shingles, infection, scars, acne, bone fractures, muscle and ligament injuries, arthritis, osteo-arthritis, rheumatiodal arthritis, skin grafts, gingival irritation, oral ulcers, dental pain and swelling, cellulitis, stretch marks, skin tone, alopecia areata, trigeminal neuralgia, herpes, zosten, sciatica, cervical erosions and other conditions."

Diamantopoulos et al teach the use of an array of substantially monochromatic radiation sources of a plurality of wavelengths, preferably of at least three different wavelengths. The sources radiate in accordance with a high duty-cycle pulsed rate, and are arranged within the array such that radiation of at least two different wavelengths passes directly or indirectly through a single point located within the treated tissue.

Use of LEDs in administering light therapy for the treatment of certain ailments and complaints is disclosed in Applicant's published UK Application GB 2212010A.

SUMMARY OF THE INVENTION

The present invention seeks to provide a method and apparatus for therapeutic illumination which are particularly suited for treatment of rhinitis. The apparatus and method of the present invention is suitable for treatment of various nasal conditions.

There is thus provided, in accordance with a preferred embodiment of the present invention, a method of treating rhinitis by illumination including the steps of:

illuminating a rhinitis affected zone of the interior of a nostril with non-coherent light radiation emitted by at least one light emitting diode (LED), the light radiation having a narrow bandwidth centered at a wavelength suitable for rhinitis treatment;

maintaining the light radiation for a prescribed treatment duration.

In a preferred embodiment of the invention, the non-coherent light radiation is continuous wave (CW) light radiation.

In a preferred embodiment of the invention, the narrow bandwidth comprises a red light bandwidth. Preferably, the red light wavelength is approximately 660 nm.

Further, in accordance with a preferred embodiment of the invention, the at least one LEDs comprises a plurality of LEDs arranged in a LED pack adapted for insertion into the rhinitis affected nostril. Preferably, the LED pack comprises at least one concentric circular arrangement of LEDs.

Additionally, in a preferred embodiment of the present invention, each of the plurality of LEDs emits a cone of light, and the method described above further includes the step of configuring and arranging the LEDs such that the plurality of cones of light emitted by the plurality of LEDs illuminate a common area of said zone.

Preferably, the rhinitis affected zone is illuminated at a power concentration level of between approximately one milliwatt per squared centimeter and approximately thirty milliwatts per squared centimeter. More preferably, the rhinitis affected zone is illuminated at a power concentration level of between approximately one milliwatt per squared centimeter and approximately thirty milliwatts per squared centimeter.

Further, in accordance with a preferred embodiment of the invention, there is provided apparatus for treating rhinitis by illumination including at least one light emitting diode (LED) pack, each having a plurality of light emitting diodes (LEDs), suitable for insertion into at least one, respective, rhinitis affected nostril and operative for illuminating a rhinitis affected zone of the interior surface of the at least one nostril with non-coherent light radiation, the light radiation having a narrow bandwidth centered at a wavelength suitable for rhinitis treatment.

In a preferred embodiment, the non-coherent light radiation is continuous wave (CW) light radiation.

Preferably, the narrow bandwidth comprises a red light bandwidth. More preferably, the red light wavelength is approximately 660 nm.

In a preferred embodiment of the invention, the LED pack comprises at least one concentric circular arrangement of LEDs. Preferably, each of the LEDs emits a cone of light and the LEDs are arranged and configured such that the plurality of cones of light illuminate a common area of said zone.

Preferably, the rhinitis affected zone is illuminated at a power concentration level of between approximately one milliwatt per squared centimeter and approximately thirty milliwatts per squared centimeter.

According to one, preferred, embodiment of the invention the apparatus for treating rhinitis further includes a support arrangement, adapted for mounting on the face of a user and operative for supporting the at least one LED pack at a position suitable for biostimulative treatment of the at least one rhinitis affected nostril.

BRIEF DESCRIPTION OF THE DRAWINGS

The present invention will be understood and appreciated more fully from the following detailed description, taken in conjunction with the following drawings in which.

DETAILED DESCRIPTION OF PREFERRED EMBODIMENTS

Figure 1:
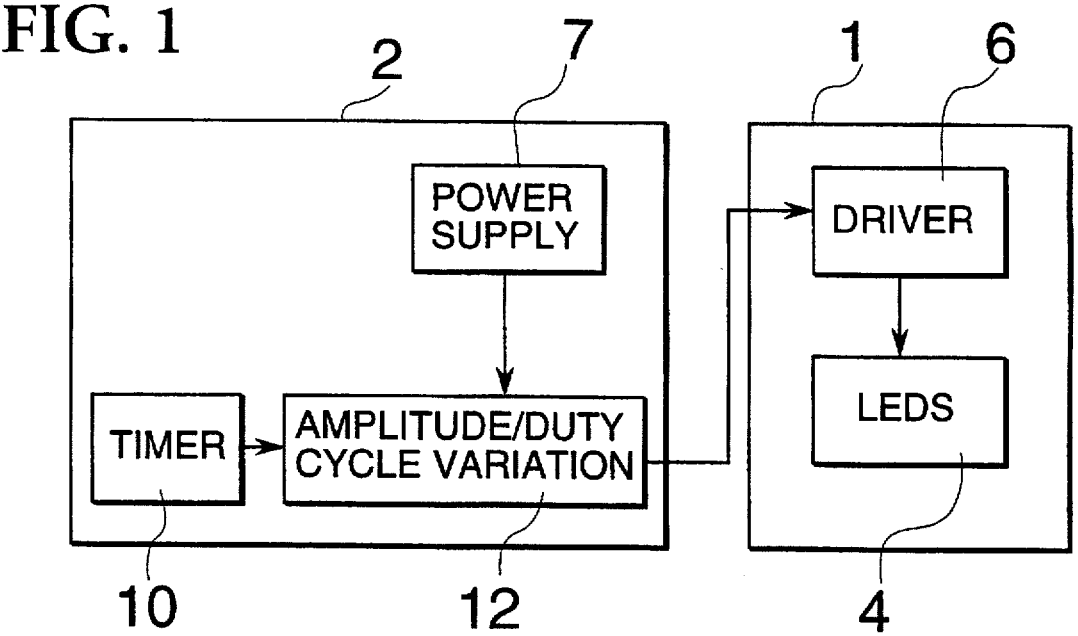
FIG. 1 is a simplified block diagram functionally showing apparatus for treating rhinitis, constructed and operative in accordance with a preferred embodiment of the present invention.

Referring to FIG. 1, there is shown a compact light source 1 and an associated control unit 2 which preferably has a CW (continuous wave) mode of operation. Light source 1 preferably comprises a plurality of light emitting diodes (LEDs) 4 which receive power via a driver circuit 6. Preferably, each of LEDs 4 emits light of substantially the same frequency.

Control unit 2 includes a power supply 7 and a timer 10 which may include a standard clock circuit provided with "set time" switches, and whose function is to disable the control circuit 2 after a preset time has elapsed. Power supply 7 preferably includes a battery, such as a lithium battery, or an AC/DC converter which draws electric power from the grid.

An amplitude and/or duty cycle variation circuit 12 provides a direct current (DC) signal with a variable amplitude and/or duty cycle which is fed to driver 6 of light source 1. Thus, light source 1 emits light continuously with a magnitude and/or duty cycle determined by amplitude/duty cycle variation circuit 12.

In a preferred embodiment of the invention, LEDs 4 are driven by driver 6 in the CW mode of operation controlled by control unit 2. Experimental results show that a pure CW mode of operation is more effective than either a PW (pulsed wave) mode of operation or any combination of the two modes.

Figure 2:
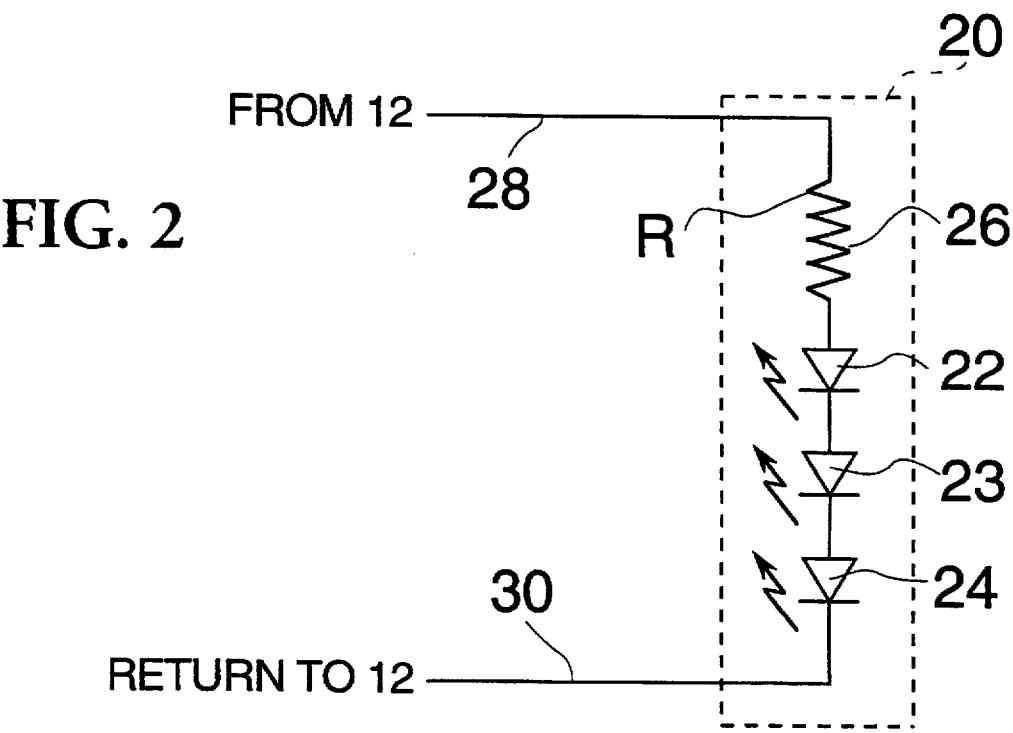
FIG. 2 shows the LEDs of FIG. 1 in greater detail.

FIG. 2 shows a preferred embodiment of LEDs 4 in detail. The LEDs 4 are arranged in the form of an LED pack 20 including a preselected number of LEDs. In the example shown in FIG. 2, LED pack 20 includes three LEDs, 22, 23 and 24, connected in series. LEDs 22, 23 and 24 are preferably connected, in series with a resistor 26 which limits the current flowing through the LEDs, between a high voltage DC rail 28 and a low voltage DC rail 30. In the example of FIG. 2, one terminal of series resistor 26 is connected to high voltage rail 28 whilst the cathode of LED 24 is connected to low voltage rail 30.

According to an alternative embodiment of the invention, series resistor 26 and power supply 7 may be replaced by a current source.

Figure 3:
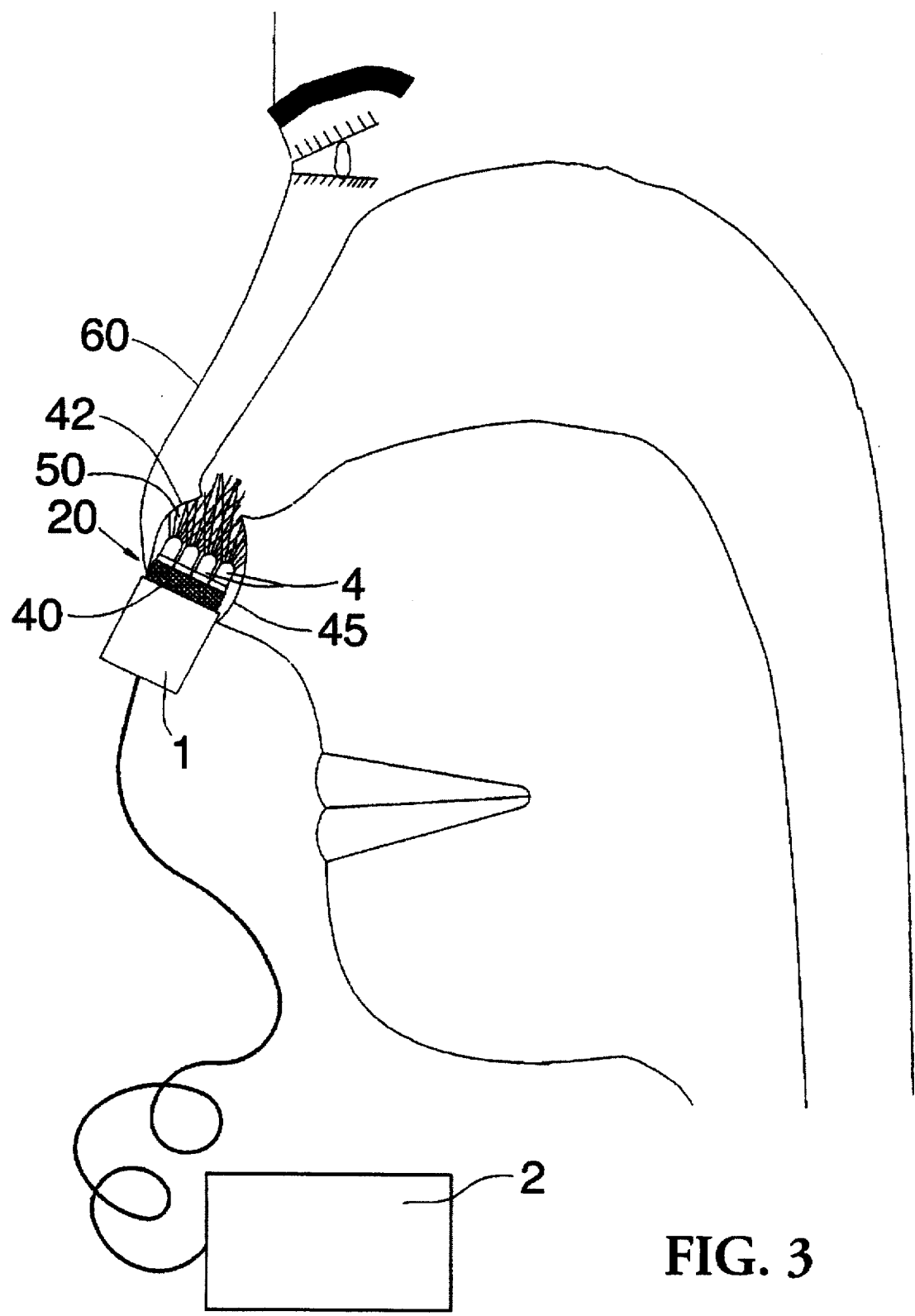
FIG. 3 is a schematic, pictorial, illustration of apparatus for treating rhinitis, constructed and operative in accordance with one preferred embodiment of the present invention.

FIG. 3 shows a preferred arrangement of LED pack 20 which is shown schematically in FIG. 2. LEDs 4 are preferably mounted on a support base 40 and arranged such that their light outputs illuminate a defined zone 42, for example a rhinitis-afflicted region of the internal surface 45 of a human nostril 50. In a preferred embodiment of the invention, zone 42 which LEDs 4 illuminate is adapted to cover most of the internal surface of a typical human nostril with substantially homogeneous illumination intensity. The LEDs may be arranged in any suitable manner on base 40, for example in one or more concentric circles. It will be understood that, generally, the number of LEDs included in LED pack 20 of FIG. 2 controls the light output intensity of light source 1 (FIG. 1).

It will be appreciated that each of LEDs 4 emits a cone of light, and the LEDs are configured and arranged such that the plurality of cones of light emitted by the plurality of LEDs intersects over zone 42, such that more than one of LEDs 4 illuminate a common area of zone 42. Preferably, every point of zone 42 is illuminated by more than one of LEDs 4.

During operation, amplitude and/or duty cycle variation circuit 12 provides a DC voltage with variable amplitude and/or duty cycle between high voltage supply rail 28 and ground terminal 30. Thus, by varying the setting of amplitude/duty cycle variation circuit 12, the overall current flowing through LED pack 20 may be varied and, thereby, the light intensity provided by light source 1 is varied. As mentioned above, it is preferred that variation circuit 12 is set to a substantially continuous-wave mode of operation.

A preferred power level is between 1–30 mW/cm$^2$, for example 10 mW/cm$^2$.

Thus, the invention affords low cost apparatus for treating rhinitis by producing a non-coherent source of illumination, preferably in CW mode, which is focussed over a predefined area. In a preferred embodiment of the invention, the exact wavelength of the illumination is confined to a relatively narrow bandwidth (±25 nm) centered at a wavelength which may be predetermined and provided by suitable selection of LEDs 4 in LED pack 20. Experimental evidence indicates that red light, particularly 660 nm light, is particularly suitable for the treatment of rhinitis. The average intensity of the emitted illumination may be varied by the operator, and the therapy duration may be preset by means of the integral timer circuit 10.

Figure 4:
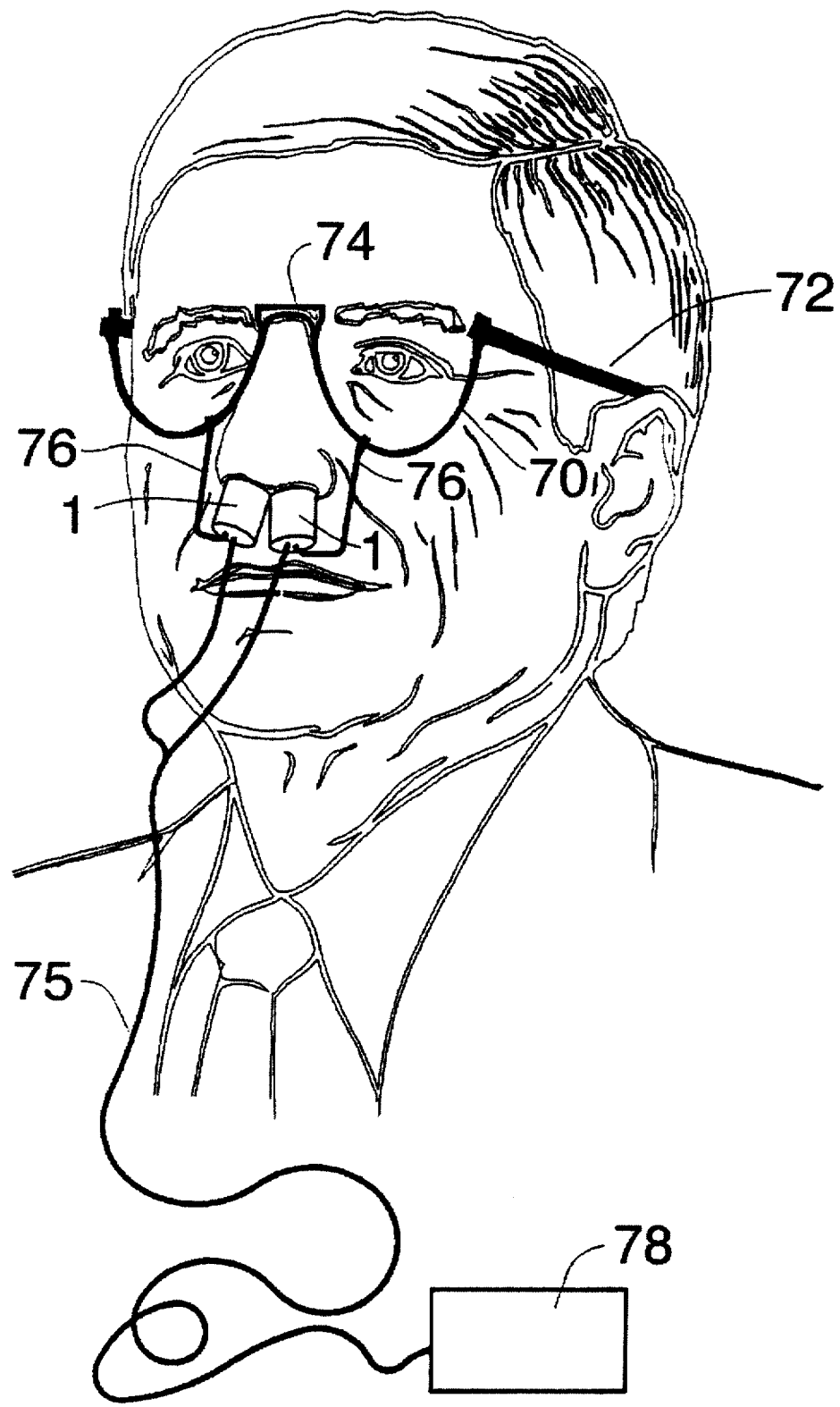
FIG. 4 is a schematic, pictorial, illustration of apparatus for treating rhinitis, constructed and operative in accordance with another preferred embodiment of the present invention.

Reference is now made to FIG. 4 which schematically illustrates an alternative, preferred, embodiment of the invention which may be particularly useful for patients requiring repeated treatment over prolonged periods of time. According to this embodiment, at least one light source 1 is securely, yet adjustably, mounted on a generally rigid support arrangement 70 which is mounted, in turn, on the face of a user. Support arrangement 70 preferably includes two ear supports 72 and a nose-top support 74, such as the ear and nose supports of eye glasses, so as to provide secure mounting of arrangement 70 on the face of the user. Each of the at least one light sources 1 is preferably mounted on an adjustable downward extension 76 of arrangement 70. FIG. 4 shows two light sources 1 mounted on two, respective, extensions 76 of arrangement 70, which are adjusted such that light sources 1 operatively engage the two nostrils of the user, respectively.

Light sources 1 are preferably powered and controlled, via suitable wires 75, by a control unit 78, similar to control unit 2 (FIGS. 1–3) but adapted to power and control more than one light source 1. Control unit 78 may be hand held or mounted to any suitable location on the user or placed at any other suitable location. Using this preferred embodiment of the invention, biostimulative illumination treatment as described above may be conveniently applied to both nostrils simultaneously.

Figure 5:
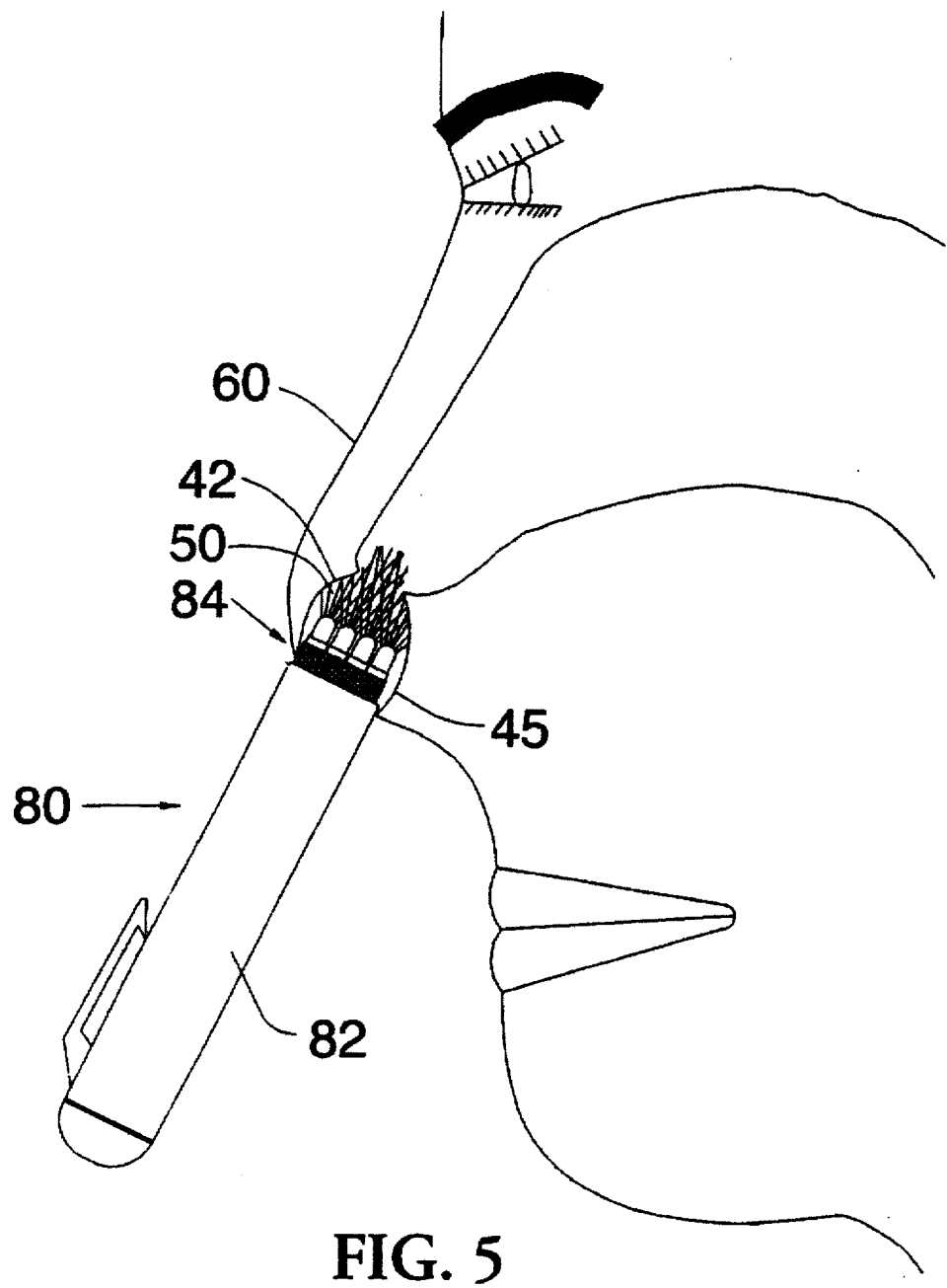
FIG. 5 is a schematic, pictorial, illustration of apparatus for treating rhinitis, constructed and operative in accordance with yet another preferred embodiment of the present invention.

Reference is now made to FIG. 5 which schematically illustrates another alternative, preferred, embodiment of the invention, wherein light source 1 and control unit 2 (FIGS. 1–3) are integrated into a single light treatment device 80. Treatment device 80 preferably includes an elongated, preferably pen-shaped, housing 82 which encloses circuitry substantially equivalent to that of control unit 2 and light source 1. A LED pack 84, which may be identical to LED pack 20 (FIG. 3), is disposed at one end of housing 82 and connected to the circuitry in housing 82 in the manner described above with reference to FIG. 2.

During operation, treatment device 80 may be hand held by the user, preferably at a prescribed position suitable for biostimulative illumination treatment. When device 80 is properly positioned, LED pack 84 operatively engages a rhinitis affected nostril for biostimulative treatment thereof, as described above with reference to FIGS. 1–3. Device 80 is preferably powered by a compact power source, such as a lithium battery.

It will be appreciated that the particular features of the methods and apparatus shown and described herein may be employed separately or in combination in any suitable manner so as to enhance efficacy of treatment.

Devices for treatment by illumination are disclosed in Published UK application GB 2212010A. However, it is believed that the embodiments described hereinabove, with reference to FIGS. 1–5, are preferred embodiments for treatment of rhinitis.

Experimental results indicate that most effective treatment of rhinitis symptoms, particularly those associated with the nostrils, is achieved when using light in the red bandwidth illuminated in a CW mode of operation. The experiments show a success rate of approximately 70 percent in relieving rhinitis symptoms, such as runny and/or itchy noses and post nasal drainage of mucus.

A preferred rhinitis treatment session, derived from actual experimental trials, will now be described. In a preferred embodiment of the invention, as shown in FIG. 3, LED pack 20 of light source 1 is preferably inserted to one of nostrils 50 of a rhinitis-suffering human nose 60 and, then, activated for a preselected treatment duration, for example three minutes. Then, light source 1 is removed from the treated nostril 50 and inserted to the other, untreated, nostril 50 for substantially the same treatment. This completes one rhinitis treatment session. For best results, the session described above is performed repeatedly, a number of times each day, over long periods of time, typically a few months.

It will be appreciated by persons skilled in the art that the present invention is not limited to what has been particularly shown and described hereinabove. Rather, the scope of the present invention is defined only by the claims that follow:

We claim:

1. A method of treating allergic rhinitis comprising the steps of:
   (a) providing at least one light emitting diode which emits non-coherent light radiation having a narrow bandwidth centered at a red light wavelength suitable for rhinitis treatment;
   (b) driving the at least one light emitting diode to emit the non-coherent light radiation;
   (c) illuminating a rhinitis affected zone of the interior of a nostril with the non-coherent light radiation without simultaneously illuminating the zone with non-coherent light emitting diode radiation in a bandwidth centered about a different wavelength; and
   (d) maintaining the light radiation for a prescribed treatment duration.

2. A method of treating allergic rhinitis in accordance with claim 1 wherein the step of providing includes providing a plurality of light emitting diodes with each light emitting diode emitting non-coherent light radiation having a narrow bandwidth centered at the same red light wavelength, the step of driving including driving the plurality of light emitting diodes, the rhinitis affected zone of the interior of a nostril having at least one common area, the step of illuminating the rhinitis affected zone comprising simultaneously illuminating the common area with light radiation from at least two of the light emitting diodes of the plurality.

3. A method of treating allergic rhinitis in accordance with claim 2 wherein the step of driving comprises driving the light emitting diodes in a continuous wave mode.

4. A method of treating allergic rhinitis in accordance with claim 2 wherein two nostrils include rhinitis affected zones, the step of illuminating comprising simultaneously illuminating a rhinitis affected zone in each nostril.

5. A method of treating allergic rhinitis in accordance with claim 1 wherein the step of driving comprises driving the at least one light emitting diode in a continuous wave mode.

6. A method of treating allergic rhinitis in accordance with claim 1 wherein the step of illuminating includes the step of positioning at least a portion of the at least one light emitting diode into the nostril.

7. A method of treating allergic rhinitis in accordance with claim 1 wherein the step of illuminating further includes the step of concentrating the emitted light radiation in the interior of the nostril.

8. A method of treating allergic rhinitis in accordance with claim 7 wherein the step of concentrating includes positioning at least a portion of the at least one light emitting diode in the interior of the nostril.

9. A method of treating allergic rhinitis in accordance with claim 1 wherein the light radiation is emitted at a narrow bandwidth centered at a wavelength of approximately 660 nm.

10. A method of treating allergic rhinitis in accordance with claim 1 wherein the step of illuminating a rhinitis affected zone includes illuminating the zone at a power concentration level of between approximately one milliwatt per square centimeter and approximately thirty milliwatts per square centimeter.

11. A method of treating allergic rhinitis in accordance with claim 1 wherein the prescribed treatment duration is in the order of three minutes.

12. A method of treating rhinitis in accordance with claim 1 wherein the narrow bandwidth is in the order of ±25 nm.

13. A biostimulative illumination system for the treatment of rhinitis, the system comprising a power source, a plurality of light emitting diodes, each diode emitting non-coherent light radiation having a narrow bandwidth centered at a red light wavelength suitable for biostimulative rhinitis treatment and a driver, the driver driving the light emitting diodes to emit the non-coherent light radiation, the power source being operatively connected to the driver and the plurality of light emitting diodes being operatively connected to the driver, the system further including a housing, the plurality of light emitting diodes being arranged at one end of the housing, wherein the plurality of diodes are arranged such that their longitudinal axes are other than diverging, with the light radiation from each diode being directed to a common zone, the plurality of diodes being dimensioned and configured to permit insertion into the base of a nostril afflicted with rhinitis, the one end of the housing emitting light radiation only from the plurality of diodes and only in the narrow bandwidth centered at the red light wavelength, the common zone comprising a rhinitis afflicted region of the nostril when said plurality of diodes are inserted into the base of the nostril.

14. A biostimulative illumination system for treatment of rhinitis as constructed in accordance with claim 13 wherein the means for driving the light emitting diodes is carried within the housing.

15. A self contained portable biostimulative illumination system for treatment of rhinitis as constructed in accordance with claim 14 wherein the power source comprises a battery and is carried within the housing, the housing being substantially cylindrical and elongate.

16. A self contained portable biostimulative illumination system for treatment of rhinitis as constructed in accordance with claim 15 wherein the elongated cylindrical housing includes a pocket clip in simulation of a pen.

17. A biostimulative illumination system for treatment of rhinitis as constructed in accordance with claim 13 further including means for supporting the housing in an operative position wherein the light emitting diodes are positioned substantially within the nostril.

18. A biostimulative illumination system for treatment of rhinitis, the system comprising light emitting diode means for generating non-coherent light radiation having a narrow bandwidth centered at a wavelength suitable for rhinitis treatment, means for carrying the light emitting diode means and hands-free support means for positioning and maintaining the light emitting diode means in a fixed position at a base of a rhinitis afflicted nostril of a user for illuminating a rhinitis affected zone of an interior of the nostril, the system further including a driver for driving the light emitting diode means to emit the non-coherent light radiation on the rhinitis affected zone of the interior of the afflicted nostril.

19. A biostimulative illumination system for treatment of rhinitis in accordance with claim 18 including further light emitting diode means for generation non-coherent light radiation having a narrow bandwidth centered at a wavelength suitable for rhinitis treatment, means for carrying the further light emitting diode means and support means including means for positioning and maintaining each light emitting diode means at a base of a separate rhinitis afflicted nostril of the user.

20. A biostimulative illumination system for treatment of rhinitis in accordance with claim 19 wherein each light emitting diode means comprises a plurality of light emitting diodes.

21. A biostimulative illumination system for treatment of rhinitis in accordance with claim 18 wherein the light emitting diode means comprises a plurality of light emitting diodes.

22. A biostimulative illumination system for the treatment of rhinitis in accordance with claim 18, the hands-free support means including means for engaging an exterior portion of the user's head an means interconnecting the engaging means and the means carrying the light emitting diode means.

23. A method of treatment rhinitis in accordance with claim 1 further including the step of:

(e) repeating step (b), step (c) and step (d) at least once during a single day.

24. A method of treating allergic rhinitis in accordance with claim 23 wherein the step of repeating step (b), step (c) and step (d) is performed several times during a single day.

25. A method of treating allergic rhinitis in accordance with claim 24 wherein the step of repeating step (b), step (c) and step (d) is performed several times during a single day over a period of at least one month.

26. A method of treating allergic rhinitis in accordance with claim 23 wherein the step of repeating step (b), step (c) and step (d) is performed until the rhinitis symptoms are alleviated.

27. A biostimulative illumination system for the treatment of rhinitis, the system comprising a power source, a plurality of light emitting diodes, each diode emitting non-coherent light radiation having a narrow bandwidth centered at a red light wavelength suitable for biostimulative rhinitis treatment and means for driving the light emitting diodes to emit the non-coherent light radiation, the power source being operatively connected to the means for driving and the plurality of light emitting diodes being operatively connected to the means for driving, the system further including a housing, means for mounting the plurality of light emitting diodes in a pack at one end of the housing, the pack having a maximum transverse dimension configured to permit insertion of the pack into a nostril afflicted with rhinitis and means for supporting the housing in an operative position, the means for supporting including ear support means for engagement with an ear of the user and means interconnecting the ear support means with the housing.

28. A biostimulative illumination system for treatment of rhinitis as constructed in accordance with claim 27 wherein the means for supporting the housing includes nose support means configured for engagement with the exterior of the user's nose adjacent a bridge portion thereof and means interconnecting the nose support means with the housing.

* * * * *